United States Patent [19]

N'Guyen et al.

[11] Patent Number: 5,250,513
[45] Date of Patent: Oct. 5, 1993

[54] ANTIOXIDANT SYSTEM BASED ON A BASIC AMINO ACID IN COMBINATION WITH A TOCOPHEROL OR DERIVATIVE THEREOF AND A NONTHIOLATED POLYPEPTIDE, AND COMPOSITIONS CONTAINING THE SAME

[75] Inventors: Quang L. N'Guyen, Antony; Francois Millecamps; Jean-Baptiste Galey, both of Paris, all of France

[73] Assignee: L'Oreal, Paris, France

[21] Appl. No.: 759,560

[22] Filed: Sep. 13, 1991

[30] Foreign Application Priority Data

Sep. 14, 1990 [FR] France ............................ 90 11384

[51] Int. Cl.⁵ ..................... A61K 37/02; A61K 37/12; A61K 37/22
[52] U.S. Cl. ............................................. 514/2; 514/8; 514/21; 514/773; 514/784; 514/785; 514/801; 514/970; 514/974
[58] Field of Search ................... 514/801, 974, 970, 2, 514/8, 12, 21, 773, 784, 785

[56] References Cited

U.S. PATENT DOCUMENTS

| | | | |
|---|---|---|---|
| 3,982,008 | 9/1976 | Amin | 426/2 |
| 4,551,480 | 11/1985 | Stiefel et al. | 514/732 |
| 4,931,278 | 6/1990 | Blost et al. | 514/960 |
| 4,996,044 | 2/1991 | Mercado et al. | 424/64 |
| 5,023,235 | 6/1991 | N'Guyen et al. | 514/18 |
| 5,114,716 | 5/1992 | N'Guyen et al. | 514/844 |

Primary Examiner—Jeffrey E. Russel
Attorney, Agent, or Firm—Cushman, Darby & Cushman

[57] ABSTRACT

An antioxidant system is based on at least one basic amino acid and includes at least one tocopherol or a derivative thereof and at least one nonthiolated polypeptide. Preferably the antioxidant system contains from 0.5 to 20 weight percent of a tocopherol or derivative thereof, 0.5 to 50 weight percent of a basic amino acid and 0.5 to 90 weight percent of a nonthiolated polypeptide. This antioxidant system is employed in cosmetic or pharmaceutical compositions.

10 Claims, No Drawings

ANTIOXIDANT SYSTEM BASED ON A BASIC AMINO ACID IN COMBINATION WITH A TOCOPHEROL OR DERIVATIVE THEREOF AND A NONTHIOLATED POLYPEPTIDE, AND COMPOSITIONS CONTAINING THE SAME

The present invention relates to a new antioxidant system based on a basic amino acid in combination with at least one tocopherol or at least one of its derivatives and at least one nonthiolated polypeptide, the use of such an antioxidant system and compositions based on a oleaginous material containing such a system and, principally, cosmetic compositions.

It is known that fatty bodies have a tendency to oxidize, even at ambient temperature, and this oxidation (or rancidness) imparts to them new properties and principally a gustative or olfactive property which is generally considered undesirable when these fatty bodies are incorporated, for example, into alimentary or cosmetic compositions.

Currently there are employed, in compositions containing fatty bodies, protective agents which, in fact, play the role of an antioxidant.

Among the known antioxidants currently employed mention can be made of ascorbic acid which acts principally by the direct absorption of oxygen. However, ascorbic acid is only very slightly soluble in fatty bodies and its use then is difficult in order to protect these fatty bodies against oxidation.

In order to solubilize the ascorbic acid molecule in fatty materials, it has been proposed to employ various ascorbyl esters such as, for example, ascorbyl stearate, palmitate or laurate; see for example the article of C.F. Bourgeois, "Revue Francaise des Corps Gras", No. 9, page 353–356 (September 1981).

It is known that, apart from their own antioxidant properties, ascorbic derivatives also have the property of improving the activity of antioxidant agents such as the tocopherols or caffeic acid and its esters by favoring the regeneration of these antioxidant agents; see for example H.S. Olcott, "Oil Soap", 18, (1941), 77, U.S. Pat. No. 2,462,663 as well as French patent application No. 75.25621 (2.282.266).

There have also been proposed various improvements of these binary antioxidant agents of the type, ascorbic derivatives plus tocopherols or ascorbic derivatives plus caffeic derivatives. These improvements envisage the addition of a third constituent so as to improve again their antioxidant effects. Among the third constituents of these ternary systems, mention can be made, principally, of p-aminobenzoic acid (U.S. Pat. No. 2,462,663), phospholipids (R.W. Riemenschneider et al, "Oil Soap", 1944, 47) and amines (Klaui, Functional (Technical) Uses of Vitamins", ed. by M. Stein, University of Nottingham Seminar Vitamins, London, England (1971) page 110), etc...

There has also been disclosed in French patent application No. 88.10295 that it is possible to considerably improve the antioxidant properties of ascorbyl esters by using these antioxidants conjointly with at least one tocopherol or a mixture of tocopherols or of caffeic acid or one of its derivatives, at least one complexing agent and at least one nonthiolated polypeptide. This system exhibits, however, some inherent disadvantages in the presence of ascorbyl esters. In effect, under certain conditions, they provoke a yellowing effect of the cosmetics.

It has now been discovered that it is possible to avoid or reduce the disadvantages of the state of the art antioxidant systems and to obtain at the same time a significant potentialization of the antioxidant effect by using a basic amino acid in combination with at least one tocopherol or a tocopherol derivative and at least one nonthiolated polypeptide.

Certain amino acids have been described as antioxidants by T. Riisom et Coll. (J.A.O.C.S. October 1980, pages 354–358).

On the other hand A. Seher et Coll. have studied the antioxidant effect of a mixture of amino acids extracted from plants (Fette Seifen Anstrichmittel, Vol. 88, No. 1, 1986, pages 1–42) and have noted that this effect is improved, principally, by the addition of α-tocopherol.

The present invention thus relates to a new antioxidant system based on at least one basic amino acid characterized by the fact that the system also includes at least one tocopherol or a tocopherol derivative and at least one nonthiolated polypeptide.

By basic amino acid is meant a natural basic amino acid such as, for example, lysine, arginine and histidine, their isomeric or racemic forms, as well as synthetic basic amino acids and derivatives of natural amino acids. Preferably, in accordance with the present invention, lysine or arginine is employed.

By the expression "tocopherol" there is meant not only α-tocopherol but also β, γ or δ tocopherol as well as their mixtures. Among the tocopherol derivatives mention can be made of the esters of tocopherol such as tocopherol acetate and tocopherol nicotinate.

The nonthiolated polypeptide of the antioxidant system according to the invention has, in a general manner, an average molecular weight ranging from about 1,000 to about 100,000. Among the polypeptides that can be employed particular mention can be made of the following:

(a) the polypeptide sold under the tradename "KERASOL" (polypeptide of soluble keratin having an average molecular weight of about 100,000) by Croda Chemicals Ltd., (b) the polypeptide sold under the tradename "Polypeptide SF" (partially neutralized animal collagen polypeptide having an average molecular weight of about 1,000) by Naarden, (c) the polypeptide sold under the tradename "Polypeptide LSN" (animal collagen polypeptide in the form of its ammonium salt containing at a maximum about 3% of inorganic salt) by Naarden, and (d) the polypeptide sold under the tradename "LACTOLAN" (polypeptide obtained starting with fresh cow's milk previously delipidated) by Laboratoires Serobiologiques of Nancy, France.

It has been noted, in a quite surprising manner, that the results of the antioxidant activity of the system according to the invention show a significant synergistic effect with respect to the components taken separately as well as with respect to binary combinations.

According to the invention, the antioxidant system is preferably constituted of:

0.5 to 20 percent of a tocopherol or a tocopherol derivative, 0.5 to 50 percent of a basic amino acid and 0.5 to 90 percent of a nonthiolated polypeptide.

The preferred ratio between the concentration of the basic amino acid and the concentration of the tocopherol ranges from 1 to 20.

The effectiveness of the antioxidant system, according to the invention, has been demonstrated by the accelerated oxidation method of vitamin F, which is a substance particularly sensitive to oxidation.

For the study, the automatic device "Rancimat" of Societe Metrohm is employed.

Mixtures are prepared of vitamin F with various amounts of a tocopherol alone, with a basic amino acid alone and with a nonthiolated polypeptide alone, as well as with binary systems of a tocopherol and a basic amino acid, a tocopherol and a nonthiolated polypeptide, or still one of a basic amino acid and a nonthiolated polypeptide. These mixtures are compared to the ternary system in accordance with the present invention as well as with a control.

Each sample is heated to 100° C., under a bubbling of air (20 liters/hour). The concentration of volatile acids resulting from the degradation of the hydroperoxides and aldehydes of vitamine F is continuously monitored in a cell filled with water in which a platinum electrode is inserted. This electrode measures, as a function of time, the increase in conductivity caused by the increase in the concentration of volatile acids. The induction time will be determined by the intersection of two asymptotes of the experimentally obtained oxidation curve.

This time corresponds t the preceding latency time of autoxidation of vitamin F. The greater the latency time is long, the better is the resistance of vitamin F to autoxidation.

The results obtained are set forth in the following table:

| Tocopherol | Basic Amino Acid (lysine) | Nonthiolated Polypeptide (Lactolan) | Induction Time (in mn) |
|---|---|---|---|
| — | — | — | 18 |
| 0.1% | — | — | 80 |
| — | 0.5% | — | 125 |
| — | — | 5% | 35 |
| 0.1% | 0.5% | — | 480 |
| — | 0.5% | 5% | 72 |
| 0.1% | — | 5% | 220 |
| 0.1% | 0.5% | 5% | 1100 |

These results clearly show the superiority of the antioxidant activity of the ternary system according to the invention with respect to the constituents taken separately, and with respect to the binary systems, tocopherol-lysine, tocopherol-nonthiolated polypeptide and lysine-nonthiolated polypeptide.

The present invention also relates to compositions containing a fatty body, characterized by the fact that the composition includes at least one antioxidant system, such as defined above.

The compositions according to the invention can principally be alimentary compositions (edible oils, lard, butter, margarine or other butter substitutes) and cosmetic or dermo-pharmaceutical compositions.

The fatty bodies present in the compositions of the invention are, for example, fatty bodies of animal origin such as cetin (spermaceti), beeswax, lanolin, perhydrosqualene, turtle oil, etc.; vegetable fatty bodies in the form of oils, fats or waxes such as sweet almond oil, avocado oil, olive oil. . . ; copra oil or hydrogenated cabbage palm oil, cocoa butter, Carnauba wax, Montan wax; as well as synthetic oils constituted by esters and/or ethers of glycerol or glycols such as, for example, those which are described in French patents Nos. 75.24656, 75.24657 and 75.24658.

In addition to the more or less oxidizable fatty bodies, the cosmetic or dermo-pharmaceutical compositions can contain products which are sensitive to oxidation such as, for example, vitamin F or $\beta$-carotene.

The compositions according to the invention are provided in the form of oily solutions, water-in-oil or oil-in-water emulsions, optionally anhydrous products, lotions or even microdispersions or ionic or nonionic lipid vesicles. They constitute principally milks for the care of the skin, creams (face creams, hand creams, body creams, sunscreen creams, make-up remover creams, foundation creams), foundation fluids, make-up remover milks, sunscreen milks, bath oils, lipsticks, eyelid make-up, deodorant sticks, etc.

For topical application, the pharmaceutical compositions according to the invention comprise vehicles and ingredients necessary to provide, for example, the composition in the form of ointments, creams, milks, pomades and oily solutions.

According to a preferred embodiment, the cosmetic or dermopharmaceutical compositions are provided in a form intended to be topically applied and, in particular, creams intended for the protection of the lipids of the skin against oxidation.

In the compositions according to the invention, the anti-oxidant system, such as defined above, is generally present such that the following proportions, with respect to the total weight of the composition, are established:

| | |
|---|---|
| Tocopherol or derivative thereof | 0.05 to 2% |
| Basic amino acid | 0.05 to 5% |
| Nonthiolated polypeptide (active material) | 0.05 to 8% |

The compositions of the invention can also contain active compounds or ingredients conventionally employed in compositions mentioned above, such as surface active agents, dyes, perfumes, astringent products, ultraviolet absorbing products, organic solvents, water, etc . . .

These compositions are prepared in accordance with conventional methods.

There are now given, as an illustration and without limitation, several examples of the antioxidant system according to the invention as well as examples of compositions containing such an antioxidant system.

EXAMPLE 1

| | |
|---|---|
| Tocopherols (mixture of $\alpha$, $\beta$ and $\delta$) | 24.5% |
| Lysine | 16.25% |
| Polypeptide, "KERASOL" (active material) | 81.30% |

EXAMPLE 2

| | |
|---|---|
| Tocopherols | 20% |
| Arginine | 40% |
| Polypeptide, "LACTOLAN" (active material) | 40% |

EXAMPLE 3

| | |
|---|---|
| Tocopherols | 8.80% |

| | |
|---|---|
| Lysine | 3.50% |
| Polypeptide, "SF" (active material) | 87.70% |

Examples of Cosmetic or Dermo-pharmaceutical Compositions

A. Anti-inflammatory cream for the treatment of eczema

| | |
|---|---|
| Magnesium lanolate | 14.4% |
| Lanolin alcohol | 3.6% |
| Turnsole oil | 40% |
| Isopropyl myristate | 8% |
| Ozokerite | 4% |
| Vitamin F | 2% |
| Hydrocortisone 17-propionate 21-acetate | 0.1% |
| Soy lecithin | 5% |
| Tocopherols | 0.15% |
| Lysine | 1% |
| Polypeptide, "KERASOL" | 5% |
| Perfume | 0.8% |
| Methyl parahydroxybenzoate | 0.3% |
| Water, sufficient amount for | 100 wt. % |

B. Body Oil

| | |
|---|---|
| Karite oil | 2% |
| Turnsole oil | 31.8% |
| Vitamin F | 2% |
| Soy oil | 32% |
| Tocopherols | 1% |
| Arginine | 2% |
| Polypeptide, "Lactolan" | 2% |
| Soy lecithin | 0.10% |
| Peanut oil, sufficient amount for | 100 wt % |

C. Fluid for the car of the body

*1st phase*

| | |
|---|---|
| Nonionic amphiphilic lipid having the general formula:<br>R—(OCH$_2$—CH)$_n$OH,<br>                        |<br>                        CH$_2$OH<br>wherein R is hexadecyl and n has an average statistical value equal to 3 | 4.5% |
| Cholesterol | 4.5% |
| Dicetylphosphate | 1% |
| Methylparahydroxybenzoate | 0.3% |
| Sterile demineralized water | 30% |

This mixture is vigorously stirred in order to obtain a homogeneous dispersion of spherules.

*2nd phase*

To the spherule dispersion obtained in the first phase the following substances are added:

| | |
|---|---|
| Perfume | 0.4% |
| Turnsole oil | 10% |
| Paraffin oil | 4% |
| Vitamin F | 2% |
| Tocopherols | 0.15% |
| Lysine | 1% |
| Polypeptide, "SF" | 3% |
| Carboxyvinyl polymer, sold under the tradename "CARBOPOL 940" by Goodrich | 0.4% |
| Triethanolamine | 0.4% |
| Demineralized water, sufficient amount for | 100% |

D. Lipsome cream

*1st phase*

| | |
|---|---|
| Hydrogenated soy lecithin, sold under the tradename "LECINOL 510" by Nikko | 1.8% |
| Cholesterol | 0.9% |
| Lipoamine-palmitoyl collagenic acid having the formula<br>CH$_3$—(CH$_2$)$_{14}$—CO—NH—CHR—COOH,<br>wherein R is the residue of amino acids obtained by hydrolysis of collagen, sold under the tradename "PCO" by Rhone Poulenc | 0.3% |
| Methylparahydroxybenzoate | 0.25% |
| Sterile demineralized water | 30% |

This mixture is vigorously stirred in order to obtain a homogeneous dispersion of spherules.

*2nd phase*

To the spherule dispersion of the first phase the following substances are added:

| | |
|---|---|
| Perfume | 0.4% |
| Karite oil | 10% |
| Almond oil | 7% |
| Cyclomethicone | 5% |
| Tocopherols | 0.15% |
| Lysine | 1% |
| Polypeptide, "LACTOLAN" | 0.5% |
| Carboxyvinyl polymer, sold under the tradename "CARBOPOL 940" by Goodrich | 0.4% |
| Triethanolamine | 0.4% |
| Sterile demineralized water, sufficient amount for | 100% |

E. Oil-in-water body milk

| | |
|---|---|
| Glycerol stearate | 2% |
| Sorbitan monostearate having 20 moles of ethylene oxide, sold under the tradename "TWEEN 60" by Atlas | 1% |
| Stearic acid | 1.4% |
| Triethanolamine | 0.7% |
| "CARBOPOL 940", neutralized by triethanolamine | 0.2% |
| Sweet almond oil | 3% |
| Petrolatum oil | 8% |
| Tocopherols | 0.1% |
| Lysine | 1% |
| Polypeptide, "LACTOLAN" | 3% |
| Preservative, sufficient amount | |
| Sterile, demineralized water, sufficient amount for | 100% |

F. Oil-in-water care cream

| | |
|---|---|
| Glycerol stearate | 2% |
| "TWEEN 60" | 1% |
| Cetyl alcohol | 0.5% |
| Stearic acid | 1.4% |
| Triethanolamine | 0.7% |
| "CARBOPOL 940", neutralized by triethanolamine | 0.4% |
| Liquid fraction of karite fat | 12% |
| Synthetic perhydrosqualene | 12% |
| Tocopherols | 0.2% |
| Arginine | 2% |
| Polypeptide, "SF" | 3% |
| Preservatives, sufficient amount | |
| Sterile, demineralized water, sufficient amount for | 100% |

We claim:

1. An antioxidant system based on (a) at least one basic amino present in an amount ranging from 0.5 to 50 weight percent, (b) at least one of a tocopherol, a tocopherol acetate or tocopherol nicotinate or a mixture thereof, present in an amount ranging from 0.5 to 20 weight percent and (c) at least one nonthiolated polypeptide present in an amount ranging from 0.5 to 90 weight percent.

2. The antioxidant system of claim 1 wherein said basic amino acid is arginine, lysine of a mixture thereof.

3. The antioxidant system of claim 1 wherein said tocopherol is selected from α-tocopherol, β-tocopherol, γ-tocopherol, δ-tocopherol or a mixture thereof.

4. The antioxidant system of claim 1 wherein said nonthiolated polypeptide has a molecular weight ranging from 1,000 to 100,000.

5. The antioxidant system of claim 1 wherein the ration of the concentration of the basic amino acid to the concentration of the tocopherol or tocopherol acetate or tocopherol nicotinate or a mixture thereof ranges from 1 to 20.

6. A cosmetic or pharmaceutical composition containing an antioxident system containing, relative to the total weight of said composition, 0.05 to 2 weight percent of a tocopherol or a tocopherol acetate or tocopherol nicotinate or a mixture thereof, 0.05 to 5 weight percent of a basic amino acid and 0.05 to 8 weight percent of a nonthiolated polypeptide. derivative thereof, 0.05 to 5 weight percent of a basic amino acid and 0.05 to 8 weight percent of a nonthiolated polypeptide.

7. The composition of claim 1 wherein said basic amino acid is lysine or arginine.

8. The composition of claim 1 wherein said tocopherol is selected from $\alpha$-tocopherol, $\beta$-tocopherol, $\gamma$-tocopherol, $\delta$-tocopherol or a mixture thereof.

9. The composition of claim 6 in the form of a cream for protecting the lipids of the skin against oxidation.

10. A composition comprising a fatty body and an antioxidant system, wherein said antioxidant system is based on (a) at least one basic amino acid present in an amount ranging from 0.05 to 50 weight percent, (b) at least one of a tocopherol, a tocopherol acetate or tocopherol nicotinate or a mixture thereof, present in an amount ranging from 0.05 to 20 weight percent and (c) at least one nonthiolated polypeptide present in an amount ranging from 0.05 to 90 weight percent.

* * * * *